(12) United States Patent
Brigmon et al.

(10) Patent No.: US 7,473,546 B2
(45) Date of Patent: Jan. 6, 2009

(54) SURFACTANT BIOCATALYST FOR REMEDIATION OF RECALCITRANT ORGANICS AND HEAVY METALS

(75) Inventors: Robin L. Brigmon, North Augusta, SC (US); Sandra Story, Greenville, SC (US); Denis Altman, Evans, GA (US); Christopher J. Berry, Aiken, SC (US)

(73) Assignee: Savannah River Nuclear Solutions, LLC, Aiken, SC (US)

( * ) Notice: Subject to any disclaimer, the term of this patent is extended or adjusted under 35 U.S.C. 154(b) by 787 days.

(21) Appl. No.: 10/712,491

(22) Filed: Nov. 13, 2003

(65) Prior Publication Data

US 2005/0106702 A1    May 19, 2005

(51) Int. Cl.
*C12N 1/12* (2006.01)
*C12N 1/20* (2006.01)

(52) U.S. Cl. ................. 435/252.1; 435/253.3; 435/829; 435/874; 435/877; 435/878; 435/880; 435/882; 435/262.5

(58) Field of Classification Search ....................... None
See application file for complete search history.

(56) References Cited

U.S. PATENT DOCUMENTS

| 3,616,204 | A | 10/1971 | Linn |
| 4,849,360 | A | 7/1989 | Norris |
| 5,024,949 | A | 6/1991 | Hegeman et al. |
| 5,100,455 | A | 3/1992 | Pinckard |
| 5,522,985 | A | 6/1996 | Bender et al. |
| 6,110,372 | A | 8/2000 | Perriello |
| 6,503,746 | B1 | 1/2003 | Daane |

FOREIGN PATENT DOCUMENTS

| RU | 2 228 953 | 5/2004 |
| WO | WO 00/56668 A | 9/2000 |

OTHER PUBLICATIONS

Heitcamp & Cerniglia, "Effects of Chemical Structure and Exposure on the Microbial Degradation of Polycyclic Aromatic Hydrocarbons in Freshwater & Estuarine Ecosystems", Env. Toxicology & Chem. vol. 6, pp. 535-546, 1987.

Dabrock et al, "Identification & Characterization of a Transmissible Linear Plasmid From *Rhodoccus erythropolis* BD2 That Encodes Isopropylbenzene & Trichlorethene Catabolism", Applied & Env. Microbiology, vol. 60, No. 3, Mar. 1994, pp. 853-860.

Rosselo-Mora et al, "Comparative Biochemical and Genetic Analysis of Naphthalene Degradation among *Pseudomonas stutzeri* Strains", Applied & Env. Microbiology, vol. 60, No. 3, Mar. 1994, pp. 966-972.

Juhasz et al, "Microbial degradation and detoxification of high molecular weight polycyclic aromatic hydrocarbons by *Stenotrophomonas maltophilia* strain VUN 10,003", Letters in App. Microbiology 2000, vol. 30, pp. 396-401.

Story et al, "Identification of four structural genes and two putative promoters necessary for utilization of naphthalene, phenanthrene, and fluoranthene by *Sphingomonas paucimobilis* var. EPA505", Gene, vol. 260, 2000, pp. 155-169.

Hammer et al, "Isolation and Characterization of a Dibenzofuran-Degrading Yeast: Identification of Oxidation and Ring Cleavage Products", App. & Env Microbiology, vol. 64, No. 6. Jun. 1998, pp. 2215-2219.

Gorden et al, "Rapid screening for bacteria capable of degrading toxic organic compounds", J of Microbiological Methods vol. 18, 1993, pp. 339-347.

Bezalel et al, "Initial Oxidation Products in the Metabolism of Pyrene, Anthracene, Fluorene, and Dibenzothiophene by the White Rot Fungus *Pleurolus ostreatus*", App & Env Microbiology, vol. 62, No. 7, Jul. 1996, pp. 2554-2559.

Smit et al, "Analysis of Fungal Diversity in the Wheat Rhizosphere by Sequencing of Cloned PCR-Amplified Genes Encoding 18S rRNA and Temperature Gradient Gel Electrophoresis", App & Env Microbiology, vol. 65, No. 6, Jun. 1999 pp. 2614-2621.

Straub et al, "Anaerobic, Nitrate-Dependent Microbial Oxidation of Ferrous Iron", App & Env Microbiology, vol. 62, No. 4, Apr. 1996, pp. 1458-1460.

Quentmeier & Friedrich, "Transfer and Expression of Degradative and Antibiotic Resistance Plasmids in Acidolphilic Bacteria", App & Env Microbiology, vol. 60, No. 3, Mar. 1994, pp. 973-978.

(Continued)

*Primary Examiner*—David M. Naff
*Assistant Examiner*—Deborah K. Ware
(74) *Attorney, Agent, or Firm*—J. Bennett Mullinax, LLC

(57) ABSTRACT

Novel strains of isolated and purified bacteria have been identified which have the ability to degrade petroleum hydrocarbons including a variety of PAHs. Several isolates also exhibit the ability to produce a biosurfactant. The combination of the biosurfactant-producing ability along with the ability to degrade PAHs enhances the efficiency with which PAHs may be degraded. Additionally, the biosurfactant also provides an additional ability to bind heavy metal ions for removal from a soil or aquatic environment.

3 Claims, No Drawings

OTHER PUBLICATIONS

Kastner et al, "Impact of Inoculation Protocols, Salinity, and pH on the Degradation of Polycyclic Aromatic Hydrocarbons (PAHs) and Survival of PAH-Degrading Bacteria Introduced into Soil", App & Env Microbiology, vol. 64, No. 1, Jan. 1998, pp. 359-362.

Grosser et al, "Indigenous and Enhanced Mineralization of Pyrene, Benzo[a]pyrene, and Carbazole in Soils", App & Env Microbiology, vol. 57, No. 12, Dec. 1991, pp. 3462-3469.

Coates et al, "Oxidation of Polycyclic Aromatic Hydrocarbons under Sulfate-Reducing Conditions", App & Env. Microbiology, vol. 62, No. 3, Mar. 1996, pp. 1099-1101.

Stapleton et al, "Biodegradation of Aromatic Hydrocarbons in an Extremely Acidic Environment", App & Env Microbiology, vol. 64, No. 11, Nov. 1998, pp. 4180-4184.

Kanaly & Harayama, "Biodegradation of High-Molecular-Weight Polycyclic Aromatic Hydrocarbons by Bacteria", J of Bacteriology, vol. 182, No. 8, Apr. 2000, pp. 2059-2067.

Gogolev & Wilke, "Combination effects of heavy metals and fluoranthene on soil bacteria", Biol Fertil Soils (1977) 25:274-278.

Eaton & Chapman, "Formation of Indigo and Related Compounds from Indolecarboxylic Acids by Aromatic Acid-Degrading Bacteria: Chromogenic Reactions for Cloning Genes Encoding Dioxygenases That Act on Aromatic Acids", J of Bacteriology, vol. 177, No. 23, Dec. 1995, pp. 6983-6988.

Zink & Lorber, Mass Spectral Identification of Metabolites Formed by Microbial Degradation of Polycyclic Aromatic Hydrocarbons (PAH), Chemosphere, vol. 31, No. 9, 1995, pp. 4077-4084.

MacGillivray & Shiaris, "Biotransformation of Polycyclic Aromatic Hydrocarbons by Yeasts Isolated from Coastal Sediments", App & Env Microbiology, vol. 59, No. 5, May 1993, pp. 1613-1618.

Trzesicka-Mlynarz & Ward, "Degradation of polycyclic aromatic hydrocarbons (PAHs) by a mixed culture and its component pure cultures, obtained from PAH-contaminated soil", Can J. Microbiology 41:470-476 (1995).

Ishida & Nakumura, "Trichloroethylene Degradation by Ralstonia sp. KN1-10A Constituitively Expressing Phenol Hydroxylase: Transformation Products, NADH Limitation, and Product Toxicity", J.Bioscience & Bioengineering, vol. 89, No. 5, 438-445, 2000.

Nakamura, Ishida & Ilzumi, "Constitutive Trichlorethylene Degradation Led by tac Promoter Chromosomally Integrated Upstream of Phenol Hydroxylase Genes of Ralstonia sp. KN1 anad Its Nucleotide Sequence Analysis", J. Bioscience & Bioengineering, vol. 89, No. 1, 47-54, 2000.

Kastner, Breuer-Jammali & Mahro, "Enumeration and characterization of the soil microflora from hydrocarbon-contaminated soil sites able to mineralize polycyclic aromatic hydrocarbons (PAH)", J. Microbiol Biotechnol (1994) 41:267-273.

Singleton, D et al: Microbial diversity in an acidic refinery sludge: Abst. Gen. Mtg. Am. Soc. Microbiology, V. 101, 2001, p. 637 & 101st Gen. Mtg. Orlando, FL May 20-24, 2001.

Plaza Grazyna et al: "Relationship between soil microbial diversity and bioremediation process at an oil refinery", ACTA Microbiologica Polonica, V. 52, No. 2, 2003, pp. 173-182.

Database WPI, Derwent Pubs., Ltd., London, GB; AN 2004-446832—Blokhin VA et al: "Strain of bacterium *Pseudomonas alcaligenes* MEV used for the removal of petroeum and its products from soil ground & surface water".

Korda, et al: "Petroleum hydrocarbon bioremediation: sampling and analytical techniques, in situ treatments and commercial microorganisms currently used", Appl. Microbiol Biotechnol (1997) 48: 677-686.

Dagher, et al: "Comparative study of five polycyclic aromatic hydrocarbon degrading bacterial strains isolated from contaminated soils", Can. J. Microbiol 43: 368-377 (1997).

Saleh et al: "Bioremediation of Petroleum Hydrocarbon Pollution", Indian Journal of Biotechnology, vol. 2, Jul. 2003, pp. 411-425.

Andreoni et al, "Bacterial communities and enzyme activities of PAHs polluted soils", Chemosphere 57 (2004) 401-412.

Hamana, et al: "Polyamine distribution profiles in newly validated genera and species within the Flavobacterum-Flexibacter-Cytophaga-Sphingobacterium complex", Microbios 106 SR, pp. 105-116, 2001 The Faculty Press, Cambridge, Great Britain.

Communication Relating to the Results of the Partial International Search, PCT/US2005/003405, ISA/EPO, Rijswijk, NL, Sep. 12, 2005, 3 pages.

SURFACTANT BIOCATALYST FOR REMEDIATION OF RECALCITRANT ORGANICS AND HEAVY METALS

STATEMENT AS TO RIGHTS TO INVENTIONS MADE UNDER FEDERALLY SPONSORED RESEARCH AND DEVELOPMENT

This invention was made with Government support under Contract No. DE-AC09-96SR18500 awarded by the United States Department of Energy. The Government has certain rights in the invention.

FIELD OF THE INVENTION

This invention is directed towards bacterial strains useful for bioremediation and processes for using the bacterial strains. In particular, it relates to unique bacterial isolates that can degrade polyaromatic hydrocarbons (PAHs) and methods to use these novel bacterial strains for bioremediation.

BACKGROUND OF THE INVENTION

Various scientific articles and patents are referred to throughout the specification. These publications are incorporated herein by reference to describe the state of the art to which this invention pertains and to provide details on standard methodologies and apparatuses which may be useful in practicing various embodiments of the present invention.

Polyaromatic hydrocarbons (PAHs) are widespread, common pollutants particularly found in association with oil refineries, certain refined petroleum products, petroleum storage locations, and petroleum spill sites. High levels of PAHs are associated with mutagenic and carcinogenic effects in humans and pose a high risk for migration to and pollution of soil and ground water sources. As a result, there has been considerable interest in techniques and processes which will degrade PAHs and related petroleum products to remediate the environment. The uses of biological agents to treat PAHs are well known within the art. U.S. Pat. No. 6,503,746 to Daane describes bacterial strains in the family Bacillaceae which are used in PAH remediation efforts.

U.S. Pat. No. 3,616,204 to Linn discloses inoculating contaminated soil with cultures of microorganisms known to degrade the unwanted contaminants. The procedure described in Linn additionally involves introducing nutritional supplements to increase the soil remediation efficiency.

U.S. Pat. No. 5,100,455 to Pickard discloses using indigenous microflora and fauna in combination with humic substrates to biologically treat soil contaminants including petroleum associated hydrocarbons.

U.S. Pat. No. 4,849,360 to Norris discloses a bioreactor for treating petroleum contaminated soil in which air is forced through the contaminated soil to facilitate the bioremediation. The bioreactor uses indigenous microflora which are supplemented with phosphorus and nitrogen nutrients.

While a variety of PAH-degrading bacteria are known and have been utilized in various applications for remediation, there remains a need for improvement in the art in terms of identifying new and useful species having novel properties which are effective for the rapid degradation of petroleum pollutants.

SUMMARY OF THE INVENTION

The present invention relates to methods for the degradation of petroleum pollutants including polyaromatic hydrocarbons (PAHs). Additionally, the present invention relates to a biotreatment process which enhances the removal of heavy metals from soil. The present invention uses isolated and purified bacterial strains of bacterial isolates from an oil refinery field. Certain of the isolates having a further ability to produce useful biosurfactants.

It is one aspect of at least one of the present embodiments of the present invention to provide isolated bacterial strains that produce biosurfactants under in situ and ex situ remediation conditions. The innate ability of the isolated and purified bacterial strains to produce biosurfactants contributes to the remediation properties of the bacteria. The biosurfactant provides increased solubility of PAHs and access of the bacteria to the PAHs, thereby increasing the efficiency of the bioremediation by the bacteria strains.

An additional aspect of at least one of the embodiments of the present invention is related to isolated and purified strains of bacteria in which the surfactant producing properties contribute to enhanced solubilization of petroleum and petroleum-derived products. The biosurfactants increase the solubilization of the petroleum products which promotes the aqueous flushing or removal of petroleum products associated with biosurfactant aggregates such as micelles and related structures. Further, the biosurfactants also increase the bioavailability of petroleum products that enhance the microbial ability to degrade contaminants. The enhanced bioavailability is beneficial to the isolated and purified strains as well as other beneficial microorganisms present in the contaminated substrate.

It is yet another aspect of at least one of the embodiments of the present invention to provide for strains of isolated and purified bacteria which degrade 2- to 3-ringed low molecular weight PAHs such as naphthalene, phenanthrene, and fluoranthene along with PAH degradation intermediates.

It is yet a further aspect of at least one of the embodiments of the present invention to provide for a strain of isolated, purified bacteria which degrades 4-ring and higher molecular weight PAHs including pyrene and fluoranthene. Typically, the 4-ring and higher PAHs are much more persistent in the environment and resistant to degradation compared to low molecular weight PAHs. Accordingly, the ability to provide strains of bacteria which degrade 4-ring and higher high molecular weight PAHs is significant.

The PAH degradation intermediates may further function as metal chelators. This chelating activity or metal complexation may assist remediation in waste containing both PAHs and metals. Additionally, at least some of the bacterial strains identified herein have an ability to degrade several different types of PAHs (including 2-, 3-, and 4-ring PAHs) in addition to the ability to degrade phenanthrene.

It is yet another aspect of at least one of the embodiments of the present invention to provide strains of isolated and purified bacteria having surfactant properties useful in the removal of metals from contaminated soil and substrates. The isolated and purified strains of bacteria produce biosurfactant monomers. The biosurfactant monomers are produced in sufficient quantity that the monomers aggregate into three-dimensional structures including micelles. The biosurfactant micelles define polar head groups which bind with metal ions in the soil. The micelles, containing the metal ions, can be removed by aqueous suspensions or flushing, thereby lowering the metal ion content of the substrate. The resulting removed metals, contained within the biosurfactant micelles, are then more easily separated and concentrated for efficient disposal or storage.

It is yet another aspect of at least one of the present embodiments of the invention to provide for isolated and purified cultures of bacteria which produce biosurfactants under constitutive conditions, the isolated strains being further able to degrade PAHs during bioremediation conditions.

It is yet another aspect of at least one of the present embodiments of the invention to provide for isolated and purified strains of bacteria having the ability to degrade a broad range of different types of PAHs under bioremediation conditions.

It is yet another aspect at least one of the present embodiments of the invention to provide for isolated and purified strains of bacteria having an ability to bring about a general reduction of total petroleum hydrocarbons (TPH). In addition, the ability of certain of the isolates to produce a biosurfactant during bioremediation conditions increases the bioavailability of petroleum hydrocarbons to other microorganisms that may be present within the contaminated soil or other waste product.

It is yet another aspect of at least one of the present embodiments of the invention to provide for isolated and purified strains of bacteria having the ability to degrade PAHs along with an ability to produce a biosurfactant during bioremediation conditions.

These and other aspects of the invention are provided by biologically pure bacterial strains for bioremediation of petroleum products and PAHs comprising isolates selected from the isolates identified in Table 2.

Other aspects of at least one embodiment of this invention include a process of bioremediation of petroleum pollutants from a contaminated environment comprising the steps of providing a supply of a substrate contaminated with a petroleum pollutant; introducing into the supply of contaminated substrate at least one bacteria isolate which metabolizes constituents of the petroleum pollutant and which further produces a biosurfactant; and, providing adequate nutrients for a treatment time sufficient for the petroleum pollutant utilizing isolate to degrade the petroleum pollution to a target concentration of 100 ppm TPH or less.

These and other features, aspects, and advantages of the present invention will become better understood with reference to the following description and appended claims.

DESCRIPTION OF PREFERRED EMBODIMENT

A fully and enabling disclosure of the present invention, including the best mode thereof, to one of ordinary skill in the art, is set forth more particularly in the remainder of the specification. Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features described as part of one embodiment can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

The present invention is directed to bacterial isolates obtained from a century-old Czechowice oil refinery in Poland. The aged sludge from the oil refinery is characterized by its acidic (pH 2) properties and contains high concentrations of PAHs along with heavy metals. Additionally, the sludge is characterized by the presence of spent catalysts, asphaltics, diatomaceous earth, silica gel, and coal fly ash, all containing high background levels of heavy metals (Pb/Cd/Zn) which have been previously deposited at the site. The collection site is from an area having approximately 120,000 tons of waste material deposited in unlined lagoons 3 meters deep covering an area of 3.8 hectares. A total of 45 bacteria, 68 fungi, and 7 yeast species were isolated from the sludge on an acidic minimum medium (pH 4) exposed to naphthalene vapor.

A subset of isolates was characterized by traditional taxonomic criteria, BIOLOG™, and analysis of SSU rRNA genes. The bacterial groups included *Proteo* bacteria, *Ralstonia, Pseudomonas,* and *Alcaligenes* species. Further characterizations of the isolates may be seen in reference to the information provided in Tables 1 and 2. The BIOLOG™ characterization protocols using minimal nutritional factors along with various organic substrates of interest are described in reference to the publication *Use of BIOLOG™ Technology for Hazardous Chemical Screening, Microbiological Techniques* 18: 329-347, 1993, and which is incorporated herein by reference.

A total of 45 bacteria, 68 fungi, and 7 yeast species were isolated using a naphthalene vapor acidic mineral salts basal growth medium. While not separately set forth, it is noted that many of the isolates have the ability to metabolize catechol and the bacterial isolates were characterized by the ability to degrade PAHs. Additionally, it is noted that the isolated and purified organisms having the ability to degrade PAHs also have the ability to degrade a variety of petroleum pollutants associated with measurements of total petroleum hydrocarbons.

As set forth below in Table 1, three bacterial species designated CZORL1B, BP20, and CZORL1Bsm, and which correspond to isolates 1 through 3 in Table 2, were observed to produce a surfactant when grown in a minimal medium containing naphthalene, phenanthrene, or fluoranthene. Nine additional strains identified in Table 1 were observed to degrade a range of PAHs indicating the isolates have a catalytic or enzymatic ability to degrade the contaminants although the additional isolates do not demonstrate an ability to produce a surfactant.

The above identified bacterial strains are grown and maintained on 1 percent peptone, trypticase, yeast extract, glucose (PTYG) plates. The bacteria were grown aerobically at 30° C. and maintained on a minimal medium at 4° C. or long-term storage in a frozen medium maintained at −70° C. or in liquid nitrogen (−196° C.).

The identification of the bacteria was made using rDNA or Fatty Acid Methyl Esters (FAME) identification protocols as set forth in the publication *Bacterial Evolution, Microbial Reviews* 51: 221-271 by C. R. Woese (1987) and which is incorporated herein by reference. Deposits of isolates 1 through 12 as identified in Table 2 were deposited with the American Type Culture Collection (ATCC), Rockville, Md., on Oct. 9, 2003, and have the indicated ATCC designation numbers. The deposit forms accompanying each of the isolate deposits as submitted to the ATCC are incorporated herein by reference.

TABLE 1

Dihydroxylating dioxygenase and 2,3 catechol dioxygenase activity and PAH degradative range of isolates.
Assayed for the following characteristics:[a]

| Isolate | indigo | meta fission | NAP | PHE | ANT | FLE | ACE | FLA | PYR |
|---|---|---|---|---|---|---|---|---|---|
| Isolated on naphthalene vapor[b] | | | | | | | | | |
| BAA-1 (PB19) | indigo | | | | | | | | |
| BAA (PB16) | indigo | | | | | | | | |
| BP19A(PB17) | indigo | | | | | | | | |
| BAB (PB14) | indigo | | | | | | | | |
| CZORL1B (KN-1)[c] | | meta fission | | | | | | | |
| BP20 CZORL1B (KN-2)[c] | | meta fission | | | | | | | |
| CZORL1Bsm (KN-3)[c] | | meta fission | | | | | | | |
| PB15 | indigo | | NAP (was designated BP20) | | | | | | |
| Isolated with phenanthrene overspray[d] | | | | | | | | | |
| BPA | indigo | | | PHE | ANT | FLE | | | |
| BPB | indigo | | | PHE | ANT | FLE | | | |
| BPC | indigo | | | PHE | ANT | FLE | | | |
| BPD | indigo | | | PHE | ANT | FLE | | | |
| BPE | indigo | | | PHE | ANT | FLE | | | |
| BPF | indigo | meta fission | NAP | PHE | ANT | FLE | ACE | FLA | PYR |
| BPG | indigo | meta fission | | | | | | | |
| BPH | indigo | meta fission | | PHE | ANT | FLE | | FLA | PYR |
| BPI | indigo | | | PHE | ANT | FLE | | | |
| BPJ | indigo | | | | ANT | FLE | | | |
| BPK | | | | PHE | ANT | FLE | | | |
| BPL | indigo | | | PHE | | FLE | | | |
| BPM | indigo | | | PHE | ANT | FLE | | | PYR |
| BPN | indigo | | | PHE | ANT | FLE | | FLA | |
| BPO | indigo | | | PHE | ANT | FLE | | | |
| BPP | indigo | | | PHE | | | | | |
| BPQ | indigo | | | PHE | ANT | FLE | | | |
| BPR | indigo | meta fission | | PHE | | | | | |

[a]Abbreviations; indigo, production of indigo from indole; meta fission, 2,3 catechol dioxygenase activity; NAP, naphthalene; PHE, phenanthrene; ANT, anthracene; FLE, fluorene; ACE, acenanphthene; FLA, fluoranthene; PYR, pyrene.
[b]Bacteria isolated on agar plates exposed to naphthalene.
[c]Bacteria produced biosurfactant
[d]Bacteria isolated on agar plates exposed to phenanthrene crystals.

TABLE 2

Isolate identification.

| Isolate | Identification | ATCC Accession Number |
|---|---|---|
| 1) CZOR-L1B (KN-1) | ALCALIGENES-PIECHAUDII SRS | PTA-5580 |
| 2) BP-20 (KN-2) | RALSTONIA PICKETTII SRS. | PTA-5579 |
| 3) CZOR-L1Bsm (KN-3) | PSEUDOMONAS-PUTIDA BIOTYPE B SRS | PTA-5581 |
| 4) BPB | FLEXIBACTER CF. SANCTI SRS | PTA-5570 |
| 5) BPC | PSEUDOMONAS FREDRIKSBERGENSIS SRS | PTA-5571 |
| 6) BPE | STAPHYLOCOCCUS WARNERI. LMG 19417 SRS | PTA-5572 |
| 7) BPF | SPHINGOMONAS SRS | PTA-5573 |
| 8) BPH | SPHINGOMONAS SP. S37 SRS | PTA-5574 |
| 9) BPI | PHYLOBACTERIUM SRS (α PROTEOBACTERIUM TA-A1) | PTA-5575 |
| 10) BPJ | SERRATIA FICARIA SRS (α PROTEOBACTERIUM TA12-21) | PTA-5576 |
| 11) BPK | AGROBACTERIUM TUMEFACIENS SRS | PTA-5577 |
| 12) BPL | RHIZOBIUM SP. SDW045 SRS | PTA-5578 |

The above identified bacteria isolates have been established as distinct species. Each of the identified isolates has PAH-degrading properties and have demonstrated an ability to reduce TPH in soil as well. In addition, certain isolates have the ability to produce a biosurfactant. Each isolate is believed novel, based upon the rDNA characterization and variations noted in Tables 1 and 2 with respect to physiological growth characteristics.

The isolates 1-3, ATCC PTA-5580 (Alcaligenes-piechaudii SRS); ATCC PTA-5579, (Ralstonia pickettii SRS); and ATCC PTA-5581 (Psuedomonas-putida Biotype B SRS) identified above, all demonstrate the ability to produce a biosurfactant, the formation of which was noted during culturing conditions. The biosurfactant exudate was evaluated for each isolate and determined to have a surface tension altering property consistent with a surfactant. Isolates 4-12 all demonstrate the ability to biodegrade a variety of PAHs (Table 1). As set forth in Example 1 below, the use of a consortium of the twelve isolates identified in Table 2 to remediate petroleum hydrocarbons contained in soil in a bioreactor remediation study results in visible quantities of biosurfactants being produced under the bioremediation conditions.

The ability of certain of the isolates to produce bioreactants is believed to enhance remediation through several different mechanisms. The production of the biosurfactant increases the biological availability of PAHs and other hydrophobic petroleum compounds. The increased biological availability includes the ability of the produced surfactant to solubilize and make available to the isolate the PAHs and other petroleum compounds. As such, the isolates' ability to produce surfactants increases the efficiency of the isolates to degrade and metabolize PAHs.

As noted in Example 1, the consortium of isolates used results in visible quantities of surfactants being produced within the soil. Biosurfactants are generally known to have a chemistry consisting of a polar head and a non-polar tail. In aqueous solutions, biosurfactants serve to reduce liquid surface tension and to facilitate the formation of an emulsion between liquids of different polarities. This ability facilitates the biosurfactants' usefulness in that hydrophobic, non-polar tail regions of the biosurfactants and biosurfactant micelles may trap oils and other petroleum compounds. The trapped oils and petroleum compounds have greater bioavailability to bacteria for biodegradation. Additionally, micelles containing trapped oils and petroleum compounds may be periodically removed or flushed from the system, thereby providing an ability to further isolate and separate petroleum compounds from the soil substrate.

Additionally, micelles formed by the biosurfactants promote the removal of metals from the soil. The hydrophilic polar head groups of micelles will bind metal and metal ions present within the soil. Once bound, the soluble nature of the micelles allows the micelles and bound metals to be collected. Once collected, the now concentrated volume of micelles and contained metals can be further treated to separate the metals from the biosurfactant.

EXAMPLE 1

A mobile bioreactor was constructed and was supplied with a four ton volume of soil contaminated with low level cesium-137 and 26,000 ppm petroleum hydrocarbons. The contaminated soil was weathered material obtained from the Savannah River Site (Aiken, S.C.). The source and make up of the petroleum products is unknown but believed to be a mixture of used motor oil and diesel fuel.

The soil was amended with a 7% bulking agent of aged compost. For each isolate, a three liter culture in log growth phase was added and distributed within the four tons of mixed waste soil. The bioreactor is equipped with a raised, secondary, perforated floor having bottom feed aeration lines which provide a continuous supply of ambient air to the bioreactor. Additionally, periodic nutrient supplements of nitrogen, potassium, and phosphorus fertilizers (10-10-10) were applied to enhance the biological activity within the bioreactor. Influent and effluent water couplings were attached. Air compressors, vacuum pumps, and a liquid pump were used to control and regulate the air and liquid flows through the bioreactor and control moisture content in the bioreactor.

The presence of low level cesium-137 limited the number and types of sampling techniques used to monitor the bioreactor and required the use of HEPA filtering with the air effluent couplings. Periodic $CO_2$ measurements indicated that, in a five-month interval, 121 pounds of petroleum products were degraded. Based upon the $CO_2$ measurements, it is conservatively estimated that the bioremediation process removed 16,000 mg/kg of petroleum contaminants from the soil during the five-month evaluation interval. It is believed that within a 14-month time interval, the four ton volume of contaminated soil will have the TPH reduced to a level less than about 100 ppm based upon an average biodegradation of 62 gm/day observed over the course of the sampling interval.

The ability of the isolates to degrade petroleum and other hydrocarbon products while producing biosurfactants offers enormous advantages in terms of efficiency and versatility of treatment protocols. For instance, it is believed that for soils contaminated solely with petroleum and petroleum by-products, the present isolates may, either individually or as a consortium, be used with conventional bioremediation techniques to improve the efficiency of degradation. As described above, the action of the biosurfactants creates a greater zone of petroleum solubility for each individual bacterium. As a result, a greater availability of petroleum products occurs. Further, to the extent the isolates form aggregate colonies, biofilms, or biosheets within portions of the soil, the surfactants are believed to substantially increase the bioavailability of the petroleum substrates for the bacterial aggregates. At the same time, the surfactants also increase the solubilization of heavy metals that may be present and provide an ability to reduce the heavy metal concentration by removal of the produced surfactants.

As seen in Example 1, the consortium of isolates provides for a bioremediation process which can achieve significant reductions in petroleum from contaminated soil. This property is particularly useful with respect to formulating disposal strategies for mixed waste in which petroleum contaminated soil and low-level radioactive material are present together. Currently, soil contaminated with low-level radioactive waste and having additional petroleum contaminants must be below regulatory limits of 1 ppm for BTEX (benzene, toluene, ethylbenzene, xylene, and 100 ppm TPH (Total Petroleum Hydrocarbons) before the soil can be classified and disposed of as a low-level radioactive waste. The cost of disposing of soil which meets the definition of a low-level radioactive waste is approximately $262 per cubic meter per year. In contrast, soil containing both low-level radioactive material and petroleum contamination in excess of the regulatory limits must be stored as a mixed waste product. The cost of storage of mixed waste soil is approximately $10,165 per cubic meter of soil per year based on yearly costs alone. The ability to treat mixed waste soils and thereby remove substantial levels of petroleum contaminants is of critical importance. Removing sufficient petroleum contaminants from a mixed waste soil allows the waste to be disposed of as a low-level radioactive waste. The resulting cost is 38 times lower than the storage cost of a mixed waste.

The use of the present inoculants is further advantageous in that, unlike some prior art techniques, the volume of amendments to the soil is kept at a minimum. Keeping the volume of soil amendments to a minimum reduces the eventual disposal costs, particularly for soil containing low-level radiation.

The present isolates are also believed useful for in situ remediation projects. The consortium of isolates may be supplied to contaminated soil using any number of conventional techniques. As needed, nutritional supplements along with the supply of oxygen in either a physical or chemical form facilitates the bioremediation activity. Given the isolates' ability to degrade PAHs as well as the desired ability to degrade petroleum hydrocarbons generally, in situ remediation using the isolates is advantageous. Additionally, the ability of certain of the isolates to produce a surfactant (biosurfactant) during soil growth conditions makes the use of certain isolates more beneficial. As noted, the biosurfactant enhances the ability to physically entrap petroleum products and heavy metals as well as providing for increased solubilization and access of petroleum hydrocarbons to both the bacterial isolates as well as native microorganisms present within the soil environment.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged, both in whole and in part. Therefore, the spirit and scope of the appended claims should not be limited to the description of the preferred versions contained therein.

That which is claimed is:

1. A biologically pure bacterial strain for bioremediation of petroleum hydrocarbons, said strain selected from the group consisting of ATCC accession numbers *Flexibacter* cf. *sancti* srs, PTA-5570; *Pseudomonas fredriksbergensis* srs, PTA-5571; *Staphylococcus warneri*. Img 19417 srs, PTA-5572; *Sphingomonas* srs, PTA-5573; *Sphingomonas* sp. s37 srs, PTA-5574; *Phylobacterium* srs, PTA-5575; *Serratia ficaria* srs, PTA-5576; *Agrobacterium tumefaciens* srs, PTA-5577; *Rhizobium* sp. sdw045 srs, PTA-5578; *Ralstonia pickettii* srs, PTA-5579; *Alcaligenes-piechaudii* srs, PTA-5580; and *Pseudomonas-putida* biotype b srs, PTA-5581.

2. A biologically pure strain and mutants thereof, having all of the identifying characteristics of said strain, wherein said strain is capable of degrading petroleum hydrocarbons, said strain being selected from the group consisting of ATCC accession numbers *Flexibacter* cf. *sancti* srs, PTA-5570; *Pseudomonas fredriksbergensis* srs, PTA-5571; *Staphylococcus warneri*. Imp 19417 srs, PTA-5572; *Sphingomonas* srs, PTA-5573; *Sphingomonas* sp. s37 srs, PTA-5574; *Phylobacterium* srs, PTA-5575; *Serratia ficaria* srs, PTA-5576; *Agrobacterium tumefaciens* srs, PTA-5577; *Rhizobium* sp. sdw045 srs, PTA-5578; *Ralstonia pickettii* srs, PTA-5579; *Alcaligenes-piechaudii* srs, PTA-5580; and *Pseudomonas-putida* biotype b srs, PTA-5581.

3. A biologically pure strain according to claim 2 wherein said hydrocarbon is a polyaromatic hydrocarbon.

* * * * *